United States Patent [19]

Gatlin et al.

[11] Patent Number: 4,547,577

[45] Date of Patent: Oct. 15, 1985

[54] PREPARATION OF (TRIFLUOROMETHYL)PYRIDINES

[75] Inventors: Janice E. Gatlin, Antioch; Mark A. VanDort, Pleasant Hill, both of Calif.; Curtis L. Volkmann, Midland, Mich.

[73] Assignee: The Dow Chemical Company, Midland, Mich.

[21] Appl. No.: 618,806

[22] Filed: Jun. 8, 1984

[51] Int. Cl.⁴ .................................... C07D 213/26
[52] U.S. Cl. .............................. 546/345; 546/346
[58] Field of Search ............... 546/345, 346; 570/145, 570/147

[56] References Cited

U.S. PATENT DOCUMENTS 3,303,197  2/1967  Haszeldine et al. ............... 546/345
4,184,041  1/1980  Nishiyama et al. ................ 71/94 X

FOREIGN PATENT DOCUMENTS 1272475  4/1972  United Kingdom ............... 546/345

Primary Examiner—Joseph Paul Brust

[57] ABSTRACT

Preparation of 3-chloro-2-fluoro-5-(trifluoromethyl)-pyridine in a liquid phase halogen exchange reaction from 2,3-dichloro-5-(trichloromethyl)pyridine in the absence of a catalyst.

7 Claims, No Drawings

PREPARATION OF (TRIFLUOROMETHYL)PYRIDINES

BACKGROUND OF THE INVENTION

The present invention relates to a method of preparing (trifluoromethyl)pyridine compounds by reacting (trichloromethyl)pyridine compounds with anhydrous hydrogen fluoride in the absence of a catalyst.

Fluorination of (trichloromethyl)pyridine compounds has been carried out by vapor phase fluorination which requires the use of high temperatures. Such vapor phase reactions suffer from disadvantages including, for example, energy costs associated with elevating the temperature of the reactants, the decomposition of starting materials and end products associated with high temperature vapor phase reaction systems and, furthermore, low conversion and/or low selectivities to the desired (trifluoromethyl)pyridine products. See, for example, Japanese Kokai Tokkyo Koho No. 80 85,564, 27 June 1980, Appl. No. 78/158,979, 22 December 1978 and U.S. Pat. Nos. 4,266,064 and 4,288,599.

U.S. Pat. No. 4,184,041 discloses a method of preparing (trifluoromethyl)pyridine compounds by reacting a (trichloromethyl)pyridine compound with gaseous hydrogen fluoride at a temperature from 0°–50° C. While this method may produce small quantities of (trifluoromethyl)pyridine compounds, it is an unacceptable commercial means of producing (trifluoromethyl)pyridine compounds.

It is clearly evident that a more efficient method of preparing (trifluoromethyl)pyridine compounds is desirable in order to commercially produce such compounds.

SUMMARY OF THE INVENTION

In accordance with the present invention, 3-chloro-2-fluoro-5-(trifluoromethyl)pyridine is prepared in a liquid phase halogen (fluorine-chlorine) exchange reaction from 2,3-dichloro-5-(trichloromethyl)pyridine in the absence of a catalyst. In a further embodiment, 2,3-dichloro-5-(trifluoromethyl)pyridine is prepared by treating the 3-chloro-2-fluoro-5-(trifluoromethyl)pyridine with HCl with or without a catalyst.

The present method is conducted by contacting the (trichloromethyl)pyridine compound with anhydrous hydrogen fluoride in the absence of a catalyst under liquid phase conditions sufficient to form the desired (trifluoromethyl)pyridine compound.

The compounds prepared by the process of this invention are useful as intermediates in the manufacture of herbicides.

The present method provides a commercially efficient means of producing (trifluoromethyl)pyridine compounds in a liquid phase reaction system. The liquid phase condition provides a reaction where the desired (trifluoromethyl)pyridine compounds are produced in a selective manner and in a reasonable time. Additionally, the present liquid phase reaction may be run continuously by the addition of starting materials to a reaction vessel while the desired (trifluoromethyl)pyridine product, which generally has a boiling point less than the temperature at which the reaction is conducted, is collected by the condensation of (trifluoromethyl)pyridine vapors.

DETAILED DESCRIPTION OF THE INVENTION

This invention provides a process for preparing 3-chloro-2-fluoro-5-(trifluoromethyl)pyridine which comprises contacting 2,3-dichloro-5-trichloromethyl-pyridine with at least a stoichiometric amount of anhydrous hydrogen fluoride at a temperature of 170° to 200° C. and a pressure of at least 200 psig in the absence of a catalyst.

The invention further provides a process wherein 2,3-dichloro-5-(trifluoromethyl)pyridine is prepared by including the sequential step of adding anhydrous HCl while maintaining the temperature at 100° to 200° C.

The (trichloromethyl)pyridine compounds, described herein are known compounds and are prepared in any of a number of well known procedures. U.S. Pat. Nos. 3,787,420; 3,743,648; 4,331,811; 4,184,081 and 3,818,019, all of which are incorporated herein by reference, disclose methods of preparing (trichloromethyl)pyridines and halo(trichloromethyl)pyridines.

Hydrogen fluoride is employed as the source of fluorine in the present reaction. The hydrogen fluoride is introduced into the present reaction as hydrogen fluoride (anhydrous). The hydrogen fluoride is bubbled into the reaction as a gas or fed into the reaction as a liquid. Hydrogen fluoride (anhydrous) has a boiling point of 19.5° C. and the liquid and gas consist of associated molecules. Hydrogen fluoride (anhydrous) is a well-known compound and commercially available, generally in cylinders and tank cars. In the practice of the present invention, hydrogen fluoride is supplied at a ratio of at least about 3 moles per mole of mono-(trichloromethyl)pyridine compound and preferably an excess of this amount is employed.

The reaction is conducted under liquid phase conditions at a temperature of about 170° to 200° C., preferably at a temperature between about 180° C. and about 190° C. The halogen exchange reaction is typically conducted in the presence of agitation sufficient to maintain an essentially homogenous mixture of the reactants and at a pressure of at least 200 psig, preferably at a pressure of 200 to 300 psig, and most advantageously at a pressure of 240 to 260 psig.

In conducting the reaction the order of addition of the reactants is not critical. Preferably, the hydrogen fluoride is added to the (trichloromethyl)pyridine compound with stirring, until the reaction is completed, generally in from about 1 to about 50 hours. The exact time that the reaction is complete will vary depending on a variety of factors, such as, temperature, HF flow rate, degree of agitation and pressure. The hydrogen fluoride is fed into the reaction mixture as a liquid or, alternatively, may be bubbled or sparged into the reaction mixture as a gas.

Higher pressures and higher hydrogen fluoride flow rates tend to decrease the reaction time. However, the use of excessive hydrogen fluoride flow rates presents several disadvantages, i.e., refluxing of liquid hydrogen fluoride tends to reduce temperature and removal and/or recovery of the excess hydrogen fluoride can be costly and/or troublesome. Flow rates of from about 0.15 to 0.45 mole/hr/mole starting pyridine preferably 0.22 to 0.31 mole/hr/mole starting pyridine are advantageously employed.

In a further embodiment of this invention, 2,3-dichloro-5-(trifluoromethyl)pyridine is prepared by reacting the 3-chloro-2-fluoro-5-(trifluoromethyl)pyridine with anhydrous HCl at a temperature of 100° to 200° C. with or without the presence of a catalyst. When no catalyst is employed in this step, pressures of from 5 psig to about 400 psig, preferably from about 25 psig to 200 psig mg may be used. When catalysts such as Lewis acid catalysts are employed, pressures of from 1 to 3 atmospheres, preferably from 1.2–1.4 atmospheres and most preferably about 1.3 atmospheres, are used.

The following examples are given to illustrate the invention and should not be construed as limiting its scope. No attempt has been made to balance any chemical equations described herein.

EXAMPLE 1

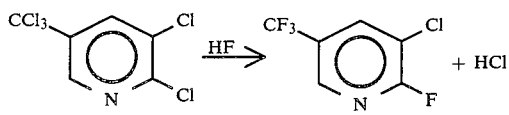

A charge of 1209.5 grams of 99 percent 2,3-dichloro-5-trichloromethylpyridine (4.52 moles) was placed in a 1-liter Hasteloy-C reactor (Parr pressure vessel) equipped for agitation and fitted with condensers, heater, pressure control and hydrogen fluoride feed. The reactor was sealed, heating and agitation begun and the pressure was held between 190–210 psig with nitrogen. When 193° C. was reached about 46 grams of hydrogen fluoride (HF) was added after which HF feed was continued at an average rate of 20 grams per hour (1.00 mole/hr/4.52 mole pyridine) while holding the temperature at 186° C., pressure at 243 psig and condensers at 12°–17° C. In 38 hours the product analyzed 83.8 wt. percent 3-chloro-2-fluoro-5-(trifluoromethyl)-pyridine and 8.0 percent of 2,3-dichloro-5-(trifluoromethyl)pyridine by GLC.

In a second step, the reactor was depressurized and flushed with nitrogen after which 5 mole percent of FeCl$_3$ was added, the pressure was held at 0–5 psig, temperatures at 138°–170° C. and anhydrous HCl was fed at a constant rate to produce 2,3-dichloro-5-(trifluoromethyl)pyridine (90 percent yield) in 23 hours. The overall yield was 85 percent in a total reaction time of 61 hours.

We claim:

1. A process for preparing 3-chloro2-fluoro-5-(trifluoromethyl)pyridine which comprises contacting 2,3-dichloro-5-trichloromethylpyridine in liquid phase with at least a stoichiometric amount of anhydrous hydrogen fluoride at a temperature of 170° fo 200° C. and a pressure of at least 200 psig in the absence of a catalyst.

2. Process of claim 1 wherein the temperature is from 180° to 190° C.

3. Process of claim 2 wherein the pressure is from 200 to 300 psig.

4. Process of claim 3 wherein the pressure is from 240 to 260 psig.

5. Process of claim 1 wherein the 3-chloro-2-fluoro-5-(trifluoromethyl)pyridine is converted to 2,3-dichloro-5-(trifluoromethyl)pyridine by the sequential step of adding anhydrous HCl while maintaining the temperature at 100° to 200° C.

6. Process of claim 5 wherein a Lewis acid catalyst is employed in the sequential step.

7. Process of claim 6 wherein the catalyst employed in the sequential step is FeCl$_3$.

* * * * *